United States Patent [19]

Ishihara et al.

[11] Patent Number: 4,769,381
[45] Date of Patent: Sep. 6, 1988

[54] NICORANDIL-CONTAINING PREPARATION FOR INJECTION

[75] Inventors: Kouji Ishihara, Saitama; Mika Sanada, Tokyo; Naoki Matsuo, Ibaraki; Yoshimitsu Iida, Saitama; Yoshinori Matsuoka; Junko Matsuo, both of Ibaraki, all of Japan

[73] Assignee: Chugai Seiyaku Kabushiki Kaisha, Tokyo, Japan

[21] Appl. No.: 3,036

[22] Filed: Jan. 13, 1987

[30] Foreign Application Priority Data

Jan. 14, 1986 [JP] Japan .................................. 61-5742

[51] Int. Cl.$^4$ .............................................. A61K 31/44
[52] U.S. Cl. ..................................... 514/355; 514/970
[58] Field of Search ................ 514/355, 356, 960, 970

[56] References Cited

U.S. PATENT DOCUMENTS

| | | | |
|---|---|---|---|
| 3,168,438 | 2/1965 | Halpern | 514/555 |
| 3,332,848 | 7/1967 | Clifton | 514/355 |
| 4,200,640 | 4/1980 | Nagano et al. | 424/266 |
| 4,323,577 | 4/1982 | Ohkuma et al. | 514/970 |
| 4,382,091 | 5/1983 | Benjamin et al. | 514/970 |
| 4,454,108 | 6/1984 | Iida et al. | 424/19 |
| 4,490,377 | 12/1984 | Chowhan | 514/970 |
| 4,565,824 | 1/1986 | Wehinger et al. | 514/356 |

FOREIGN PATENT DOCUMENTS 0185347 12/1985 European Pat. Off. .

OTHER PUBLICATIONS

Chem. Abst. 88:22652h (1978)–Nagano et al.
Chem. Abst. 99:58932v (1983)–Chugai Pharm.
Patent Abstracts of Japan, vol. 2, No. 52 (C-78)[183], 14th Apr. 1978; & JP-A-No. 53 9323.
Kirk–Othmer, *Encyclopedia of Chemical Technology*, vol. 8, Third Edition, pp. 109–110.

*Primary Examiner*—Douglas W. Robinson
*Attorney, Agent, or Firm*—Browdy and Neimark

[57] ABSTRACT

A non-liquid type preparation for injection that has improved stability contains N-(2-hydroxyethyl)-nicotinamide nitrate ester (generally known as nicorandil) and an inorganic or organic acid and/or an alkaline metal salt thereof. These ingredients, together with an excipient that is pharmaceutically acceptable, may be dissolved in a solvent, sterilized by filtration and freeze-dried to obtain a freeze-dried preparation, or may be dissolved in a solvent under an aseptic condition and recrystallized to obtain an injectable powder. Nicorandil preparations according to the present invention are very stable and useful in clinical applications.

4 Claims, No Drawings

NICORANDIL-CONTAINING PREPARATION FOR INJECTION

The present invention relates to an N-(2-hydroxyethyl)-nicotinamide nitrate ester (generally known as nicorandil)-containing preparation for injection. More particularly, the present invention pertains to a nicorandil-containing non-liquid type preparation for injection that has improved stability.

Nicorandil has coronary vasodilative, peripheral circulation improving and antispasmodic actions and is widely used in tablet form for ischemic heart disease treatment, particularly for remission or prevention of anginose attack. Nicorandil also has antiarrhythmia and cerebral circulation improving actions and it is therefore expected that it may be effectively used as a nicorandil-containing preparation for injection which may be used to improve the systemic circulation state of a patient undergoing a surgical operation and for treating patients suffering from cerebral disease in an acute condition.

However, nicorandil involves the following disadvantages. Since nicorandil has a nitric ester group, nicorandil preparations are not stable in aqueous solutions in the same manner as other drugs that have nitric ester groups, and consequently a nicorandil preparation in an aqueous solution causes a decomposition reaction which starts with hydrolysis of the nitric ester. Nicorandil preparations also cause a polymerization reaction on heating. For these reasons, it has heretofore been impossible to form a stable nicorandil-containing preparation for injection.

The present inventors therefore made various studies with a view to improving the stability of nicorandil-containing preparations for injection. As a result, the inventors found that a nicorandil-containing preparation for injection that has excellent stability can be obtained by using an inorganic or organic acid and/or an alkaline metal salt thereof as a stabilizer and forming the preparation to be of the non-liquid type. The present invention has been accomplished on the basis of this finding.

Thus, the present invention provides a nicorandilcontaining non-liquid type preparation for injection which contains an inorganic or organic acid and/or an alkaline metal salt thereof.

Examples of the inorganic acid or alkaline metal salt thereof that may be used in the present invention include phosphoric acid, carbonic acid, etc., or alkaline metal salts thereof, preferably Na and K salts thereof. Examples of the organic acid or alkaline metal salt that may be used in the present invention are acetic acid, propionic acid, butyric acid, oxalic acid, malonic acid, succinic acid, glutaric acid, adipic acid, maleic acid, fumaric acid, tartaric acid, citric acid, alginic acid, glutamic acid, etc., or alkaline metal salts thereof, preferably Na and K salts thereof.

Particularly preferable inorganic acids or alkaline metal salts thereof are phosphoric acid and carbonic acid or Na and K salts thereof, and particularly preferable organic acids are citric acid, malonic acid, succinic acid, fumaric acid, oxalic acid, tartaric acid, maleic acid and salicylic acid or Na or K salts thereof. These inorganic or organic acids and/or alkaline metal salts thereof may be employed alone or in the form of a mixture consisting of two or more selected from among the above-described substances.

The proportion of the inorganic or organic acid and/or alkaline metal salt thereof to be blended with the ether component is generally from 10% to 1,000%, preferably from 50% to 500%, relative to the amount of nicorandil. If the proportion of the stabilizer is less than 10%, the stability of the resultant nicorandil preparation will not be improved satisfactorily. Any proportion exceeding 1,000% fails to provide any greater improvement in the stability of the nicorandil preparation.

In the preparation for injection according to the present invention, an excipient, a solubilizer, an osmotic pressure adjustor, a pH adjustor and the like, provided that they are pharmaceutically permissible, may be employed according to need. Examples of excipients that may be used in the present invention include mannitol, inositol, glucose, lactose, dextran, etc. As the solubilizer, it is possible to use cyclodextrin, lecithin, macrogoal, polyoxyethylene sorbitan monolaurylate, polyoxyethylene stearic acid, triglyceride, HC0-60, etc.

Examples of suitable osmotic pressure adjustors are sodium chloride, potassium chloride, sodium bromide, sorbitol, glucose, etc.

Examples of suitable pH adjustors are citric acid, tartaric acid, sodium hydroxide, etc.

The preparation for injection according to the present invention may be produced by any known method. Above all, the freeze-drying method and the powder packing method are preferable. According to the freeze-drying method, nicorandil, an inorganic or organic acid and/or an alkaline metal salt thereof as a stabilizer, and additives including an excipient, etc. are dissolved in an appropriate solvent and sterilized by filtration. Thereafter, the solution is frozen to remove water or the solvent by means of sublimation. The nicorandil may be crystallized during the freeze-drying operation, or may be left in an amorphous state.

In the powder packing method, nicorandil which has been recrystallized in advance under an aseptic condition is blended, in an aseptic environment, with additives including an excipient, etc. and an inorganic or organic acid and/or an alkaline metal salt thereof as a stabilizer which have been sterilized by heating, filtration or a sterilizing gas separately from the nicorandil, and the blend is packed in a suitable vessel to obtain a nicorandilcontaining preparation.

The preparation for injection according to the present invention shows substantially no degradation of the pharmacological action due to decomposition of nicorandil even when it is stored for a long period of time. Thus, it is possible, according to the present invention, to obtain a nicorandil-containing preparation for injection that has greatly improved stability.

The following examples are provided for the purpose of further illustrating the present invention but are not to be construed as limiting.

EXAMPLE 1

Nicorandil (0.2 g), sodium citrate (0.5 g) and mannitol (3 g) were dissolved in 100 ml of distilled water for injection. After filtration for sterilization, the solution was pipetted into vials, 1 ml for each, and then freeze-dried by a conventional method to obtain a freeze-dried preparation.

EXAMPLE 2

Nicorandil (0.2 g), sodium citrate (0.5 g) and mannitol (3 g) were dissolved in a solvent under an aseptic condition and recrystallized, and 37.0 mg of the crystals thus formed was packed into each of the vials to obtain an injectable powder.

EXAMPLE 3

An injectable powder was obtained in the same way as in Example 2 except that the sodium citrate (0.5 g) employed in Example 2 was replaced by sodium carbonate (0.5 g).

EXAMPLE 4

A freeze-dried preparation was obtained in the same way as in Example 1 except that the sodium citrate (0.5 g) employed in Example 1 was replaced by sodium maleate (0.5 g).

EXAMPLE 5

A freeze-dried preparation was obtained in the same way as in Example 1 except that the sodium citrate (0.5 g) employed in Example 1 was replaced by sodium malonate (0.5 g).

EXAMPLE 6

A freeze-dried preparation was obtained in the same way as in Example 1 except that the sodium citrate (0.5 g) employed in Example 1 was replaced by fumaric acid (0.2 g).

EXAMPLE 7

A freeze-dried preparation was obtained in the same way as in Example 1 except that the sodium citrate (0.5 g) employed in Example 1 was replaced by oxalic acid (0.2 g).

EXAMPLE 8

An injectable powder was obtained in the same way as in Example 2 except that the sodium citrate (0.5 g) employed in Example 2 was replaced by salicylic acid (0.2 g).

COMPARATIVE EXAMPLE 1

A freeze-dried preparation having no stabilizer added thereto was obtained in the same way as in Example 1 except that the system did not use sodium citrate (0.5 g) as in Example 1.

COMPARATIVE EXAMPLE 2

A injectable powder having no stabilizer added thereto was obtained in the same way as in Example 2 except that the system did not use sodium citrate (0.5 g) as in Example 2.

EXPERIMENTAL EXAMPLE

The preparations for injection which were obtained in Examples 1 to 8 and Comparative Examples 1 and 2 were stored in a constant temperature bath at 40° C., and the time-dependent change of the residual amounts of nicorandil was measured by HPLC. The results are shown in Table 1 wherein the numerals indicate the residual amounts of nicorandil in each preparation as a percentage of the initial weight. As will be clear from Table 1, it is confirmed that the preparations according to the present invention exhibit excellent stability.

TABLE 1

| Samples | Residual nicorandil (%) | |
|---|---|---|
| | 15 days at 40° C. | 30 days at 40° C. |
| Example 1 | 96.5 | 89.0 |
| 2 | 99.7 | 92.1 |
| 3 | 98.8 | 93.2 |
| 4 | 98.0 | 90.2 |
| 5 | 98.5 | 92.0 |
| 6 | 96.8 | 90.9 |
| 7 | 95.6 | 91.1 |
| 8 | 98.2 | 93.5 |
| Comparative Example 1 | 28.9 | 0 |
| 2 | 92.3 | 75.0 |

We claim:

1. A pharmaceutical powder which comprises N-(2-hydroxyethyl)-nicotinamide nitrate ester in admixture with at least about 10%, based on the weight of the nitrate ester, of a member selected from the group consisting of phosphoric acid, carbonic acid, acetic acid, propionic acid, butyric acid, oxalic acid, malonic acid, succinic acid, glutaric acid, adipic acid, maleic acid, fumaric acid, tartaric acid, citric acid, alginic acid, glutamic acid, and sodium or potassium salts thereof.

2. A freeze-dried composition which comprises N-(2-hydroxyethyl)-nicotinamide nitrate ester in admixture with at least about 10%, based on the weight of the nitrate ester, of a member selected from the group consisting of phosphoric acid, carbonic acid, acetic acid, propionic acid, butyric acid, oxalic acid, malonic acid, succinic acid, glutaric acid, adipic acid, maleic acid, fumaric acid, tartaric acid, citric acid, alginic acid, glutamic acid, and sodium or potassium salts thereof, and an excipient selected from the group consisting of mannitol, inositol, glucose, lactose and dextran, these ingredients having been previously dissolved in a solvent, sterilized by filtration and freeze-dried.

3. A pharmaceutical powder which comprises N-(2-hydroxyethyl)-nicotinamide nitrate ester in admixture with at least about 10%, based on the weight of the nitrate ester of a member selected from the group consisting of phosphoric acid, carbonic acid, acetic acid, propionic acid, butyric acid, oxalic acid, malonic acid, succinic acid, glutaric acid, adipic acid maleic acid, fumaric acid, tartaric acid, citric acid, alginic acid, glutamic acid, and sodium or potassium salts thereof, and an excipient selected from the group consisting of mannitol, inositol, glucose, lactose and dextran, these ingredients having been previously dissolved in a solvent under an aseptic condition and recrystallized.

4. A method for producing a freeze-dried composition which comprises the steps of:
dissolving in a solvent N-(2-hydroxyethyl)-nicotinamide nitrate ester, at least about 10%, based on the weight of the nitrate ester, of a member selected from the gorup consisting of phosphoric acid, carbonic acid, acetic acid, propionic acid, butyric acid, oxalic acid, malonic acid, succinic acid, glutaric acid, adipic acid, maleic acid, fumaric acid, tartaric acid, citric acid, alginic acid, glutamic acid, and sodium or potassium salts thereof, and an excipient selected from the group consisting of mannitol, inositol, glucose, lactose and dextran;
sterilizing the solution by filtration; and
freeze-drying the sterilized solution.

* * * * *